(12) United States Patent
Zara

(10) Patent No.: US 7,999,945 B2
(45) Date of Patent: Aug. 16, 2011

(54) OPTICAL COHERENCE TOMOGRAPHY / ACOUSTIC RADIATION FORCE IMAGING PROBE

(75) Inventor: Jason Michael Zara, Vienna, VA (US)

(73) Assignee: The George Washington University, Washington, DC (US)

( * ) Notice: Subject to any disclaimer, the term of this patent is extended or adjusted under 35 U.S.C. 154(b) by 449 days.

(21) Appl. No.: 12/175,985

(22) Filed: Jul. 18, 2008

(65) Prior Publication Data

US 2009/0116032 A1 May 7, 2009

Related U.S. Application Data

(60) Provisional application No. 60/950,603, filed on Jul. 18, 2007.

(51) Int. Cl.
*G01B 9/02* (2006.01)
(52) U.S. Cl. ...................................................... 356/479
(58) Field of Classification Search ................ 356/451, 356/456, 479, 497, 502, 477; 602/22
See application file for complete search history.

(56) References Cited

U.S. PATENT DOCUMENTS

| | | | | |
|---|---|---|---|---|
| 5,944,687 A * | 8/1999 | Benett et al. | ........................ | 604/22 |
| 6,039,691 A | 3/2000 | Walker et al. | | |
| 6,104,942 A * | 8/2000 | Kruger | ........................ | 600/407 |
| 6,134,003 A * | 10/2000 | Tearney et al. | ................ | 356/479 |
| 6,405,069 B1 * | 6/2002 | Oraevsky et al. | ............. | 600/407 |
| 6,485,413 B1 * | 11/2002 | Boppart et al. | ............... | 600/160 |
| 6,501,551 B1 * | 12/2002 | Tearney et al. | ................ | 356/477 |
| 6,875,176 B2 | 4/2005 | Mourad et al. | | |
| 7,022,077 B2 | 4/2006 | Mourad et al. | | |
| 7,044,908 B1 * | 5/2006 | Montalbo et al. | ............. | 600/160 |
| 7,190,464 B2 * | 3/2007 | Alphonse | ........................ | 356/479 |
| 7,309,335 B2 * | 12/2007 | Altshuler et al. | ............... | 606/11 |
| 7,338,439 B2 * | 3/2008 | Kanai | ............................ | 600/176 |
| 7,349,098 B2 * | 3/2008 | Li | .................................. | 356/479 |
| 7,366,376 B2 * | 4/2008 | Shishkov et al. | ............... | 385/35 |
| 7,382,949 B2 * | 6/2008 | Bouma et al. | .................... | 385/25 |
| 7,420,724 B2 | 9/2008 | Smith et al. | | |
| 7,447,408 B2 * | 11/2008 | Bouma et al. | ................. | 385/123 |
| 7,486,405 B2 * | 2/2009 | Hogan | ........................... | 356/497 |

(Continued)

FOREIGN PATENT DOCUMENTS

WO WO 98/55025 12/1998

(Continued)

OTHER PUBLICATIONS

E. Bossy, A.R. Funke, K. Daoudi, A.G. Boccara, M. Tanter and M. Fink, Transient optoelastography in optically diffusive media, Applied Physics Letters 90, (2007), pp. 1174111-1-1174111-3.

(Continued)

*Primary Examiner* — Gregory J Toatley
*Assistant Examiner* — Scott M Richey
(74) *Attorney, Agent, or Firm* — Blank Rome LLP

(57) ABSTRACT

A combined system and method synchronizes optical coherence tomography and acoustic radiation force for simultaneously imaging and mechanically displacing tissue in a patient as a detection and analytic tool. An endoscope is provided which has a piezoelectric element and an OCT scanner. The piezoelectric element generates the acoustic force to displace the tissue. The OCT scanner images the tissue and the system determines the mechanical displacement of the tissue. Cancer and arterial plaques can be recognized from the mechanical displacement of the tissue.

8 Claims, 1 Drawing Sheet

U.S. PATENT DOCUMENTS

| | | | |
|---|---|---|---|
| 7,538,859 B2 * | 5/2009 | Tearney et al. | 356/35.5 |
| 7,573,627 B2 | 8/2009 | Mills et al. | |
| 7,649,630 B2 * | 1/2010 | Hogan | 356/497 |
| 7,733,497 B2 * | 6/2010 | Yun et al. | 356/497 |
| 7,809,226 B2 * | 10/2010 | Bouma et al. | 385/123 |
| 7,842,006 B2 * | 11/2010 | Wang et al. | 604/22 |
| 2002/0095087 A1 | 7/2002 | Maurad et al. | |
| 2003/0135101 A1 | 7/2003 | Webler | |
| 2004/0127782 A1 | 7/2004 | Sfez et al. | |
| 2004/0171981 A1 * | 9/2004 | Rabiner et al. | 604/20 |
| 2005/0015009 A1 | 1/2005 | Mourad et al. | |
| 2005/0148899 A1 | 7/2005 | Walker et al. | |
| 2005/0154381 A1 * | 7/2005 | Altshuler et al. | 606/9 |
| 2006/0058608 A1 | 3/2006 | Hogan | |
| 2006/0063985 A1 | 3/2006 | Hogan | |
| 2006/0079773 A1 | 4/2006 | Mourad et al. | |
| 2006/0089548 A1 | 4/2006 | Hogan | |
| 2006/0094958 A1 | 5/2006 | Marquart et al. | |
| 2006/0170930 A1 * | 8/2006 | Li | 356/479 |
| 2006/0285189 A1 | 12/2006 | Mills et al. | |
| 2007/0016031 A1 | 1/2007 | Mourad et al. | |
| 2007/0066887 A1 | 3/2007 | Mire et al. | |
| 2008/0228073 A1 | 9/2008 | Silverman et al. | |
| 2009/0116032 A1 * | 5/2009 | Zara | 356/477 |
| 2009/0323076 A1 * | 12/2009 | Li et al. | 356/479 |

FOREIGN PATENT DOCUMENTS

| | | |
|---|---|---|
| WO | WO 02/43564 | 6/2002 |
| WO | WO 02/059580 | 8/2002 |
| WO | WO 03/057018 | 7/2003 |
| WO | WO 2004/002305 | 1/2004 |
| WO | WO 2004/107963 | 12/2004 |
| WO | WO 2006/023614 | 3/2006 |
| WO | WO 2006/023634 | 3/2006 |
| WO | WO 2006/047388 | 5/2006 |
| WO | WO 2006/060107 | 6/2006 |
| WO | WO 2007/038135 | 4/2007 |

OTHER PUBLICATIONS

G. Van Soest, R. R. Bouchard, F. Mastik, N. De Jong, and A. F.W. Van Der Steen, Robust intravascular optical coherence elastography driven by acoustic radiation pressure, SPIE vol. 6627, edited by P.E. Andersen, A. Chen, pp. 66270E-1-66270E-10, copyright 2007.

* cited by examiner

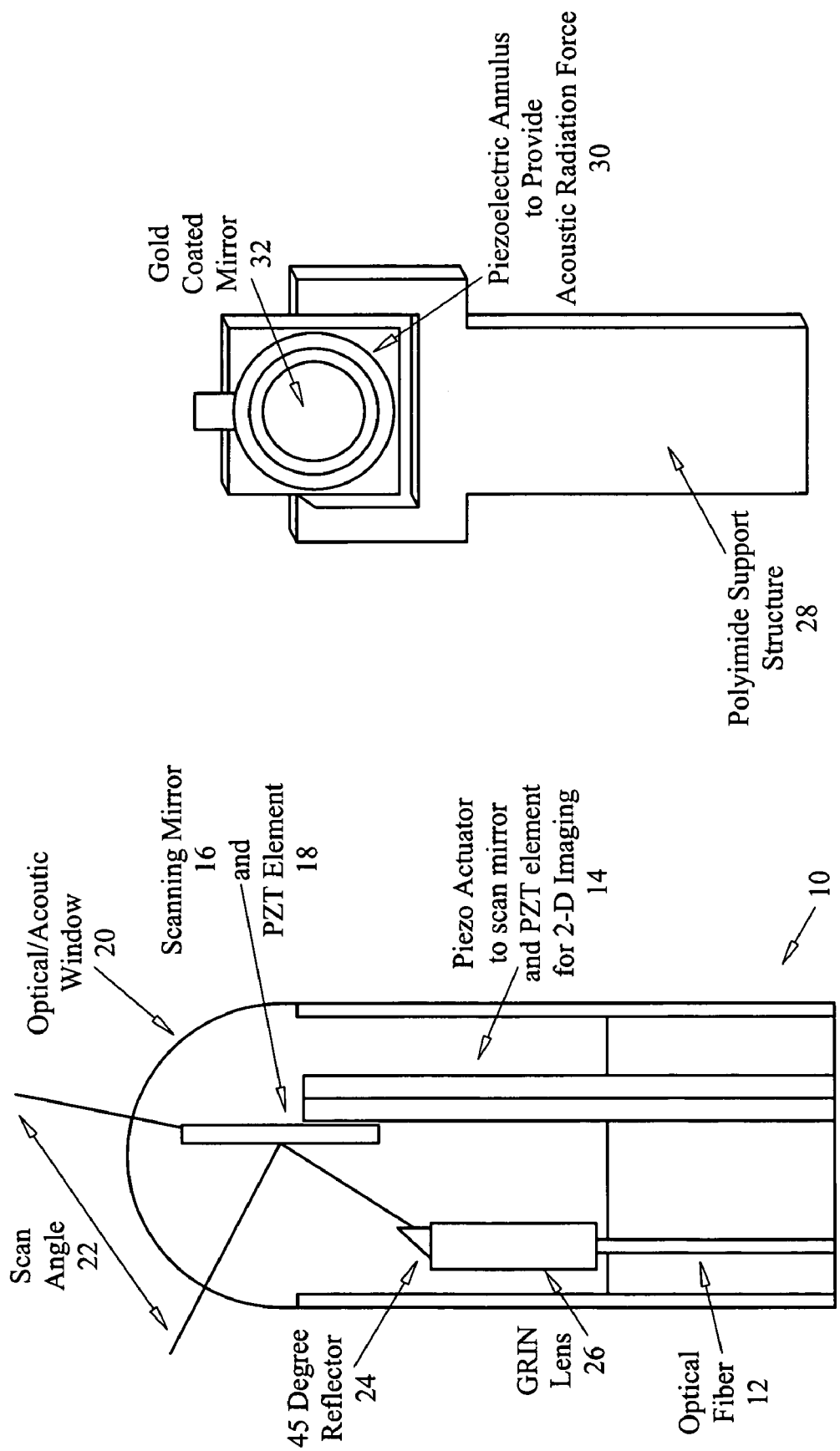

OPTICAL COHERENCE TOMOGRAPHY / ACOUSTIC RADIATION FORCE IMAGING PROBE

RELATED APPLICATION INFORMATION

This application claims priority benefit under 35 U.S.C. 119(e) to U.S. provisional 60/950,603 file 18 Jul. 2007, incorporated by reference herein in its entirety.

STATEMENT OF GOVERNMENTAL INTEREST

The U.S. Government has no interest in this invention by virtue of a grant.

FIELD OF THE INVENTION

The field of the invention is medical imaging, and more specifically the invention relates to a combined system which synchronizes optical coherence tomography and acoustic radiation force for simultaneously imaging and mechanically displacing tissue in a patient as a detection and analytic tool. Detection of cancer and arterial plaques are primary targets of interest.

BACKGROUND

OCT Probes

Optical coherence tomography apparatus are fairly well known and comprise a low coherent light source and an optical interferometer, commonly designed as either a Michelson optical fiber interferometer or a Mach-Zender optical fiber interferometer.

For instance, an optical coherence tomography apparatus known from the paper by X. Clivaz et al., "High resolution reflectometry in biological tissues", OPTICS LETTERS, Vol. 17, No. 1, Jan. 1, 1992, includes a low coherent light source and a Michelson optical fiber interferometer comprising a beam-splitter optically coupled with optical fiber sampling and reference arms. The sampling arm incorporates an optical fiber piezoelectric phase modulator and has an optical probe at its end, whereas the reference arm is provided with a reference mirror installed at its end and connected with a mechanical in-depth scanner which performs step-by-step alteration of the optical length of this arm within a fairly wide range (at least several tens of operating wavelengths of the low coherent light source), which, in turn, provides information on microstructure of objects at different depths. Incorporating a piezoelectric phase modulator in the interferometer arm allows for lock-in detection of the information-carrying signal, thus providing a fairly high sensitivity of measurements.

The apparatus for optical coherence tomography reported in the paper by J. A. Izatt, J. G. Fujimoto et al., Micron-resolution biomedical imaging with optical coherence tomography, Optics & Photonics News, October 1993, Vol. 4, No. 10, p. 14-19 comprises a low coherent light source and an optical fiber interferometer designed as a Michelson interferometer. The interferometer includes a beam-splitter, a sampling arm with a measuring probe at its end, and a reference arm, whose end is provided with a reference mirror, movable at constant speed and connected with an in-depth scanner. This device allows for scanning the difference in the optical lengths of the sampling and reference arms. The information-carrying signal is received in this case using a Doppler frequency shift induced in the reference arm by a constant speed movement of the reference mirror.

Another optical coherence tomography apparatus comprising a low coherent light source and an optical fiber interferometer having a beam-splitter optically coupled to a sampling and reference arms is known from RU Pat. No. 2,100, 787, dated 1997. At least one of the arms includes an optical fiber piezoelectric in-depth scanner, allowing changing of the optical length of said interferometer arm by at least several tens of operating wavelengths of the light source, thus providing information on microstructure of media at different depths. Since piezoelectric in-depth scanner is a low-inertia element, this device can be used to study media whose characteristic time for changing of optical characteristics or position relative to the optical probe is very short (the order of a second).

A major disadvantage inherent in all of the above-described apparatus as well as in other known apparatus of this type is that studies of samples in the direction approximately perpendicular to the direction of propagation of optical radiation are performed either by respective moving of the samples under study or by scanning a light beam by means of bulky lateral scanners incorporated into galvanometric probes. This does not allow these devices to be applied for medical diagnostics of human cavities and internal organs in vivo, as well as for industrial diagnostics of hard-to-access cavities.

Apparatus for optical coherence tomography known from U.S. Pat. No. 5,383,467, 1995 comprises a low coherent light source and an optical interferometer designed as a Michelson interferometer. This interferometer includes a beam-splitter, a sampling arm with an optical fiber sampling probe installed at its end, and a reference arm whose end is provided with a reference mirror connected with an in-depth scanner, which ensures movement of the reference mirror at a constant speed. The optical fiber sampling probe is a catheter, which comprises a single-mode optical fiber placed into a hollow metal tube having a lens system and an output window of the probe at its distal end. The optical tomography apparatus includes also a lateral scanner, which is placed outside the optical fiber probe and performs angular and/or linear scanning of the optical radiation beam in the output window of the optical fiber probe. However, although such geometry allows for introducing the probe into various internal cavities of human body and industrial objects, the presence of an external relative to the optical fiber probe lateral scanner and scanning the difference in the optical lengths of the sampling and reference arms by means of mechanical movement of the reference mirror significantly limit the possibility of using this device for performing diagnostics of surfaces of human cavities and internal organs in vivo, as well as for industrial diagnostics of hard-to-access cavities.

Apparatus for optical coherence tomography known from U.S. Pat. No. 5,582,171, 1996 comprises a low coherent light source and an optical fiber interferometer designed as a Mach-Zender interferometer having optical fiber sampling and reference arms and two beam-splitters. The reference arm includes a unit for changing the optical length of this arm. This unit is designed as a reference mirror with a spiral reflective surface arranged with a capability of rotating and is connected with a driving mechanism that sets the reference mirror in motion. The sampling arm is provided with an optical fiber probe having an elongated metal cylindrical body with a throughhole extending therethrough, and an optical fiber extending through the throughhole. A lateral scanner is placed at the distal end of the probe, which lateral scanner comprises a lens system, a rotatable mirror, and a micromotor for rotating the mirror, whereas an output window of the probe is located in the side wall of the cylindrical body. This device allows imaging of walls of thin vessels, but is unsuitable as a diagnostic means to image surfaces of cavities and internal organs inside a human body, as well as for industrial diagnostics of hard-to-access large-space cavities.

Another optical coherence tomography apparatus is known from U.S. Pat. No. 5,321,501, 1994 and comprises a low coherent light source optically coupled with an optical fiber Michelson interferometer, which includes a beam-splitter and optical fiber sampling and reference arms. The reference arm has a reference mirror mounted at its end and connected with an in-depth scanner. The latter performs movement of the reference mirror at a constant speed, thereby changing the optical length of this arm by at least several tens of operating wavelengths of the light source. The interferometer also comprises a photodetector whose output is connected with a data processing and displaying unit, and a source of control voltage connected with the in-depth scanner. The sampling arm incorporates an optical fiber probe having an elongated body with a throughhole extending therethrough, wherein a sheath with an optical fiber embedded in it extends through the throughhole. The sheath is attached to the stationary body through a pivot joint. The probe body contains also a lateral scanner comprising a bearing support, an actuator, and a lens system. The actuator includes a moving part and a stationary part, whereas the bearing support, the stationary part of the actuator and the lens system are mechanically connected with the probe body. The fiber-carrying sheath rests on the moving part of the actuator. The actuator may be a piezoelectric element, stepper motor, electromagnetic system or electrostatic system. The distal part of the probe body includes a lens system, the end face of the distal part of the optical fiber being optically coupled with the lens system, whereas the actuator is connected with a source of control current. The output of the data processing and displaying unit of the optical fiber interferometer is the output of the apparatus for optical coherence tomography. A disadvantage of this apparatus is that it is not fit for diagnostics of surfaces of hard-to-access internal human organs in vivo, such as, for example, stomach and larynx, and for industrial diagnostics of surfaces of hard-to-reach cavities of technical objects. That is due to the fact that the optical fiber probe in this apparatus must have relatively large dimensions since maximum movement of the optical fiber relative to the size of the actuator cannot be more than 20%, because of the moving part of the actuator being positioned at one side of the fiber-carrying sheath. Besides, the mechanical movement of the reference mirror at a constant speed used for scanning the difference in optical lengths of the reference and sampling arms restricts the range of objects, which can be studied in vivo by this apparatus, or by any other apparatus of this kind, to those objects whose optical characteristics and position relative to the optical probe do not change practically in the process of measurements.

Particular attention was also given to studies of biological tissues in vivo. For instance, a method for studying biological tissue in vivo is known from U.S. Pat. No. 5,321,501, 1994 and U.S. Pat. No. 5,459,570, 1995, in which a low coherent optical radiation beam at a given wavelength is directed towards a biological tissue under study, specifically ocular biological tissue, and to a reference mirror along the first and the second optical paths, respectively. The relative optical lengths of these optical beam paths are changed according to a predetermined rule; radiation backscattered from ocular biological tissue is combined with radiation reflected from a reference mirror. The signal of interference modulation of the intensity of the optical radiation, which is a result of this combining, is used to acquire an image of the ocular biological tissue. In a particular embodiment, a low coherent optical radiation beam directed to biological tissue under study is scanned across the surface of said biological tissue.

A method for studying biological tissue in vivo is known from U.S. Pat. No. 5,570,182, 1996. According to this method, an optical radiation beam in the visible or near IR range is directed to dental biological tissue. An image is acquired by visualizing the intensity of scattered radiation. The obtained image is then used for performing diagnostics of the biological tissue. In a particular embodiment, a low coherent optical radiation beam is used, which is directed to dental tissue, said beam being scanned across the surface of interest, and to a reference mirror along the first and second optical paths, respectively. Relative optical lengths of these optical paths are changed in compliance with a predetermined rule; radiation backscattered from the dental tissue is combined with radiation reflected by the reference mirror. A signal of interference modulation of intensity of the optical radiation, which is a result of said combining, is used to visualize the intensity of the optical radiation backscattered from said biological tissue. However, this method, as well as other known methods, is not intended for performing diagnostics of biological tissue covered with epithelium.

Acoustic Radiation Force Imaging

Ultrasound imaging is a non-invasive, diagnostic modality that is capable of providing information concerning tissue properties. In the field of medical imaging, ultrasound may be used in various modes to produce images of objects or structures within a patient. In a transmission mode, an ultrasound transmitter is placed on one side of an object and the sound is transmitted through the object to an ultrasound receiver. An image may be produced in which the brightness of each image pixel is a function of the amplitude of the ultrasound that reaches the receiver (attenuation mode), or the brightness of each pixel may be a function of the time required for the sound to reach the receiver (time-of-flight mode). Alternatively, if the receiver is positioned on the same side of the object as the transmitter, an image may be produced in which the pixel brightness is a function of the amplitude of reflected ultrasound (reflection or backscatter or echo mode). In a Doppler mode of operation, the tissue (or object) is imaged by measuring the phase shift of the ultrasound reflected from the tissue (or object) back to the receiver.

Ultrasonic transducers for medical applications are constructed from one or more piezoelectric elements activated by electrodes. Such piezoelectric elements may be constructed, for example, from lead zirconate titanate (PZT), polyvinylidene diflouride (PVDF), PZT ceramic/polymer composite, and the like. The electrodes are connected to a voltage source, a voltage waveform is applied, and the piezoelectric elements change in size at a frequency corresponding to that of the applied voltage. When a voltage waveform is applied, the piezoelectric elements emit an ultrasonic wave into the media to which it is coupled at the frequencies contained in the excitation waveform. Conversely, when an ultrasonic wave strikes the piezoelectric element, the element produces a corresponding voltage across its electrodes. Numerous ultrasonic transducer constructions are known in the art.

When used for imaging, ultrasonic transducers are provided with several piezoelectric elements arranged in an array and driven by different voltages. By controlling the phase and amplitude of the applied voltages, ultrasonic waves combine to produce a net ultrasonic wave that travels along a desired beam direction and is focused at a selected point along the beam. By controlling the phase and the amplitude of the applied voltages, the focal point of the beam can be moved in a plane to scan the subject. Many such ultrasonic imaging systems are well known in the art.

An acoustic radiation force is exerted by an acoustic wave on an object in its path. The use of acoustic radiation forces produced by an ultrasound transducer has been proposed in connection with tissue hardness measurements. See Sugimoto et al., "Tissue Hardness Measure Using the Radiation Force of Focused Ultrasound", IEEE Ultrasonics Symposium, pp. 1377-80, 1990. This publication describes an experiment in which a pulse of focused ultrasonic radiation is applied to deform the object at the focal point of the transducer. The deformation is measured using a separate pulse-echo ultrasonic system. Measurements of tissue hardness are made based on the amount or rate of object deformation as the acoustic force is continuously applied, or by the rate of relaxation of the deformation after the force is removed.

These and other documents may provide additional context where necessary for fuller understanding of the claimed invention and are incorporated by reference herein in their entirety for references purposes and for assisting in the determination of the level of ordinary skill in the art, e.g. U.S. Pat. No. 7,022,077.

SUMMARY

In one preferred embodiment, a combined system is provided which synchronizes optical coherence tomography and acoustic radiation force for simultaneously imaging and mechanically displacing tissue in a patient, which comprises an endoscopic probe having i) means for delivering infrared light for OCT imaging and ii) a piezoelectric transducer for delivering acoustic radiation force to target tissue.

In another preferred embodiment, a method of obtaining mechanical properties of target tissue in a patient is provided, comprising simultaneously imaging said tissue using optical coherence tomography while subjecting said target tissue to mechanical displacement using acoustic radiation force.

In another preferred embodiment, a method of detecting cancer within target tissue in a patient is provided, comprising simultaneously imaging said tissue using optical coherence tomography while subjecting said target tissue to mechanical displacement using acoustic radiation force, and comparing the imaging and displacement data to control data.

In another preferred embodiment, a method of detecting whether an arterial plaque in a patient is solid or liquid filled is provided, comprising simultaneously imaging said tissue using optical coherence tomography while subjecting said target tissue to mechanical displacement using acoustic radiation force, and comparing the imaging and displacement data to control data.

In another preferred embodiment, a system is provided comprising an acoustic radiation force component which is operationally synchronized with an OCT component, the acoustic radiation force component comprising an acoustic source and an acoustic detector, the acoustic source and detector being operably connected to a power source, the power source being operably connected to a function generator, and the function generator being operably connected to a controller having data acquisition, storage and analysis capability, the controller having the capability to process acquired acoustic data, make determinations of at least one of acoustic emission properties, induced and intrinsic tissue displacements and relate the determination of at least one of acoustic emission properties, induced and intrinsic tissue displacement(s) with at least one physiological tissue condition of a target tissue, the controller being operably connected to a display device for displaying information relating to the at least one physiological tissue condition, and the OCT component comprising an apparatus for optical coherence tomography comprising a low coherent light source; an optical fiber interferometer, including a beam-splitter, a sampling and reference optical fiber arms, and a photodetector, which are mutually optically coupled, a data processing and displaying unit, a reference mirror being placed at the end of said reference arm, the output of said photodetector being connected with said data processing and displaying unit, and a source of control voltage, whereas the output of said data processing and displaying unit of said optical fiber interferometer is the output of said apparatus for optical coherence tomography; at least one of said arms comprising an in-depth scanner having a capability of changing the optical length of said arm by at least several tens of operating wavelengths of said light source, said in-depth scanner being controlled by a source of control voltage, said sampling arm including a flexible part, which is made capable of being introduced into an instrumental channel of an endoscope or borescope and being provided with an optical fiber probe; said optical fiber probe being designed miniature and including a lens system.

In another preferred embodiment, the system comprises wherein a part of said sampling arm of said interferometer, including said part that is made capable of being introduced into an instrumental channel of an endoscope or borescope, is made changeable and is connected by a detachable connection with a main part of said sampling arm.

In another preferred embodiment, the system comprises, wherein said changeable part of said sampling arm of said interferometer is made disposable.

In another preferred embodiment, the system comprises, wherein the distal part of said optical fiber probe is made with changeable tips.

FIGURE CAPTIONS

FIG. 1 is a graphical representation of one embodiment of the tip of the probe.

FIG. 2 is a graphical representation of the polyimide substrate.

DETAIL DESCRIPTION

While the methods and systems of the present invention may be embodied in a variety of different forms, the specific embodiments shown in the figures and described herein are presented with the understanding that the present disclosure is to be considered exemplary of the principles of the invention, and is not intended to limit the invention to the illustrations and description provided herein.

The invention involves an imaging probe that combines Optical Coherence Tomography imaging with Acoustic Radiation Force to investigate the mechanical properties of epithelial tissue to search for cancer. Acoustic radiation force from a piezoelectric transducer can be used to mechanically palpate tissues by pushing on them without physical contact. OCT imaging can then be used to image the displacements of the tissues to infer mechanical properties which may be indicative of cancerous and precancerous conditions. The primary use of the invention is to detect and diagnose cancers in epithelial tissues using this probe delivered via endoscopic method. Additional potential application include the investigation of arterial plaques to determine if they are solid or fluid filled which can be an indication of the likelihood of the plaque rupturing leading to sudden cardiac events. The scope of the invention includes both the concept of using OCT elastography to track tissue motion resulting from the application of acoustic radiation force and the infrared light for OCT imaging. A diagram representing one potential implementation method is below. In this realization, the mirror to deliver infrared light for OCT imaging and the piezoelectric transducer to deliver the acoustic radiation force are placed on a polyimide support structure which is scanned using a piezoelectric bimorph. There are numerous other possible methods to scan the imaging and acoustic force beams.

Referring now to the figures, FIG. 1 shows probe (10) having optical fiber (12), piezo actuator (14), scanning mirror (16), PZT element (18), optical/acoustic window (20), scan angle (22), 45 degree reflector (24), and GRIN lens (26).

FIG. 2 shows polyimide support structure (28) having piezoelectric annulus (30), and gold-coated mirror (32).

Acoustic Radiation Force

In one preferred embodiment, a clinically realizable ultrasound system is provided in accordance with the present invention. In this regard, the system includes a programmable function generator which generates a series of sinusoidal pulses for transmission. After generation by the function generator, the transmit pulses will be amplified by a power amplifier. The amplified pulses will then be applied to a piezoelectric transducer which converts the amplified pulses to a series of acoustic pulses. The transducer is placed against the surface of a patient's epithelial tissue. At least one of the pulses, most preferably the leading pulse which is used as a control, is of sufficient intensity and duration to cause motion of the tissue resulting from acoustic radiation force. That is, at least one of the applied acoustic pulses is of sufficient intensity and duration to cause physical displacement of the tissue target.

Acoustic echoes received by the transducer will be amplified using an amplifier and acquired with a data acquisition system. Data will be processed by a computer and displayed by a suitable display system. Data may also be stored by the computer for later use. On receiving the echo pulses, isolation from the low output impedance transmit amplifier is provided by a diode circuit between the amplifier and the transducer.

The use of algorithms employed in the ultrasonic imaging art, such as cross-correlation, auto-correlation, CW Doppler, sum absolute difference, and the like, may be employed in order to determine tissue displacements. The technique of false peak correction may be used to improve data accuracy. Two dimensional and three dimensional motion tracking methods may also be used to determine displacements. Furthermore, the display of displacement data may be in an image format with displacement magnitude mapped onto the appropriate location in the image. A map of time constant or other viscoelastic properties may also be useful.

Those in this art may find it advantageous to use a different frequency and/or focal distance for imaging than is used to generate the radiation force necessary to cause tissue displacement.

In practice, the ultrasonic transducer that is used to generate an ultrasonic pulse of sufficient magnitude to cause soft tissue displacement during an imaging sequence is most preferably moved from one position relative to the tissue under investigation to another position after each ultrasound cycle. Alternatively, for ultrasound systems utilizing linear or phased array transducers, the effective aperture may be electronically steered or electronically translated between multiple locations. In this way, data may be acquired at each tissue location that can be transformed into two- or three-dimensional images. Furthermore, it may also be desirable that the tissue be "preloaded" prior to data acquisition. That is, the ultrasound transducer may be operated in such a manner that several cycles of the application and relaxation of ultrasound force is applied to the tissue under investigation.

As noted above, according to the present invention, at least one relatively high intensity acoustic pulse may precede a series of relatively low intensity acoustic pulses. The relatively high intensity acoustic pulse serves to induce physical displacement of the target tissue. The echo from the relatively high intensity acoustic pulse also provide a control against which following echo pulses may be compared. The relatively low intensity acoustic pulses, on the other hand, provide measurement signals to allow measurement of the magnitude of the physical displacement. Alternatively, high intensity pulses may be used both to produce and observe motion. Most preferably, the present invention will intermittently perturb the body by providing an intermittent series of relatively high intensity pulses interspersed with a series of relatively low intensity pulses. In such a manner, therefore, the tissue will be physically displaced in a discontinuous manner, and the magnitude and/or time course (i.e., the frequency or rate of change) of such discontinuous physical displacement or movement can be sensed by the echoes from the intermediate relatively low intensity pulses. The frequency or time course of application of high intensity pulses may be used to selectively interrogate the low frequency response of tissue. This yields data regarding the viscoelastic properties of the tissue, rather than simply the elastic properties.

Ultrasound detection techniques are preferred for many embodiments. Ultrasound sources and detectors may be employed in a transmission mode, or in a variety of reflection or scatter modes, including modes that examine the transference of pressure waves into shear waves, and vice versa. Ultrasound detection techniques may also be used to monitor the acoustic emission(s) from insonified tissue. Detection techniques involving measurement of changes in acoustic scatter, particularly backscatter, or changes in acoustic emission, are particularly preferred for use in methods and systems of the present invention. Exemplary acoustic scatter or emission data that are related to tissue properties include: changes in scatter or acoustic emission, including changes in the amplitude of acoustic signals, changes in phase of acoustic signals, changes in frequency of acoustic signals, changes in length of scattered or emitted signals relative to the interrogation signal, changes in the primary and/or other maxima and/or minima amplitudes of an acoustic signal within a cardiac and/or respiratory cycle; the ratio of the maximum and/or minimum amplitude to that of the mean or variance or distribution of subsequent oscillations within a cardiac cycle, changes in temporal or spatial variance of scattered or emitted signals at different times in the same location and/or at the same time in different locations, all possible rates of change of endogenous brain tissue displacement or relaxation, such as the velocity or acceleration of displacement, and the like. Multiple acoustic interrogation signals may be employed, at the same or different frequencies, pulse lengths, pulse repetition frequencies, intensities, and the multiple interrogation signals may be sent from the same location or multiple locations simultaneously and/or sequentially. Scatter or emission from single or multiple interrogation signals may be detected at single or at multiple frequencies, at single or multiple times, and at single or multiple locations.

Acoustic scatter and/or emission data from selected target tissue site(s), or derivative determinations such as tissue displacement, tissue stiffness, and the like, are related, using empirical formulations and/or mathematical models, to a useful tissue property or clinical parameter. In general, higher tissue stiffness and/or lower compliance indicates a higher relative clinical parameter, while lower tissue stiffness and/or higher compliance indicates a relatively lower clinical parameter. Similarly, localized differences and/or changes in acoustic scatter and/or emission that are related to tissue stiffness properties are indicative of localized conditions such as tumors or other masses, or the presence or progression of arterial cardiovascular plaques. Supplemental data, such as noninvasive measures of mean and/or continuous arterial blood pressure and tracking of the cardiac and/or respiratory cycles, may be used in combination with acoustic data to assess clinical parameters or tissue conditions.

In both "active" and "passive" modes, single or multiple interrogation signals administered from different places and/or at different times may insonify single or multiple target tissue sites. Acoustic properties of the insonated target tissue may be assessed, by acquiring scatter or emission data, simultaneously and/or sequentially, to evaluate intrinsic and/or induced tissue displacement, or associated biological responses. In some embodiments, the absolute values for intrinsic and/or induced tissue displacement may be useful, while in other embodiments, intrinsic and/or induced tissue displacement determinations are evaluated by comparison of acquired data to empirically determined standards, by comparison to data acquired from different target tissue sites at the same or different time points, and/or by comparison to data acquired from target tissue sites over time. Active and passive modes may be used separately, or in combination, to assess target tissues.

In general, acoustic interrogation pulses have larger peak positive pressure, have a higher frequency, and are shorter than acoustic palpation pulses. Acoustic interrogation pulses, for example, may have a typical frequency between 0.5 and 15 MHz, use from 1-50 cycles per pulse, consist of 3-10,000 pulses per second, and have a time-averaged intensity of less than 0.5 W/cm.sup.2. Acoustic palpation signals may, for example, have a frequency of from 0.5 to 10 MHz, consist of long tone bursts of from 0.1-100 ms, consist of 1-100 pulses per second, and have a time averaged intensity of less than 100-1000 W/cm.sup.2, where longer pulses have lower intensities, for example. Acoustic emissions from palpated or oscillated tissue are expected to be in the frequency range of 500 Hz to 10 KHz.

Commercially available components may be used in systems of the present invention. The following description of specific components is exemplary, and the systems of the present invention are in no way limited to these components. High intensity focused ultrasound transducers are available from Sonic Concepts, Woodinville, Wash. Multi-element transducers have been used by researchers and are described in the literature. A multiple focused probe approach for high intensity focused ultrasound-based surgery is described, for example, in Chauhan S, et al., Ultrasonics 2001 January, 39(1):33-44. Multi-element transducers having a plurality of annular elements arranged, for example, co-axially, are suitable. Such systems may be constructed by commercial providers, such as Sonic Concepts, Woodinville, Wash., using technology that is commercially available. Amplifiers, such as the ENI Model A-150, are suitable and are commercially available. Diplexers, such as the Model REX-6 from Ritec, are suitable and are commercially available. Function generators, such as the Model 33120A from HP, are suitable and are commercially available. Many types of controllers are suitable and are commercially available. In one configuration, a Dell Dimension XPS PC incorporates a Gage model CS8500 A/D converter for data acquisition, and utilizes LabView software from National Standards for data acquisition and equipment control. In some embodiments, an ATL transcranial Doppler probe, Model D2TC, is used for detection.

During application of the radiation force and deformation, or shortly following application of the radiation force, another diagnostic probe pulse may be used to quantify an aspect of the deformation and, hence, provide information concerning tissue properties

OCT

Optical coherence tomography (OCT) is an interferometric, non-invasive optical tomographic imaging technique offering millimeter penetration (approximately 2-3 mm in tissue) with micrometer-scale axial and lateral resolution. The technique was first demonstrated in 1991 with ~30 μm axial resolution. Since then, OCT has achieved sub-micrometer resolution in 2001 due to introduction of wide bandwidth light sources (sources emitting wavelengths over a ~100 nm range).

OCT is based on low-coherence interferometry. In conventional interferometry with long coherence length (laser interferometry), interference of light occurs over a distance of meters. In OCT, this interference is shortened to a distance of micrometers, thanks to the use of broadband light sources (sources that can emit light over a broad range of frequencies). Light with broad bandwidths can be generated by using superluminescent diodes (superbright LEDs) or lasers with extremely short pulses (femtosecond lasers). White light is also a broadband source with lower powers.

Light in an OCT system is broken into two arms—a sample arm (containing the item of interest) and a reference arm (usually a mirror). The combination of reflected light from the sample arm and reference light from the reference arm gives rise to an interference pattern, but only if light from both arms have traveled the "same" optical distance ("same" meaning a difference of less than a coherence length). By scanning the mirror in the reference arm, a reflectivity profile of the sample can be obtained (this is time domain OCT). Areas of the sample that reflect back a lot of light will create greater interference than areas that don't. Any light that is outside the short coherence length will not interfere. This reflectivity profile, called an A-scan contains information about the spatial dimensions and location of structures within the item of interest. A cross-sectional tomograph (B-scan) may be achieved by laterally combining a series of these axial depth scans (A-scan). En face imaging (C-scan) at an acquired depth is possible depending on the imaging engine used.

A typical OCT probe comprises a probe having a lens at the distal end of optical fiber. The probe also includes a pivotal mirror and a focusing lens which operates to focus a beam to one or more optical fibers in an optical fiber bundle. The output from the fiber bundle passes through a lens and then another lens before being directed to a sample. The fiber bundle and outer catheter constitute a catheter assembly. Appropriate movement of mirror permits sample to be scanned by a beam.

Example

Acoustic Radiation Force

Acoustic pulses are applied and echoes acquired using a custom ultrasound system. 8 cycle, 5.0 MHz pulses are transmitted at a repetition rate of 12 kHz. A 5.0 mHz focused piston transducer with a focal radius of 50.8 mm and a diameter of 9.5 mm is used for acoustic transmission and reception. The transducer is excited by eight cycle sinusoidal bursts with peak amplitudes of roughly sixty volts.

The radio frequency (rf) data acquired from the transducer following the initiation of acoustic transmission showed that the echoes moved away from the transducer when transmission is initiated, but that the motion stops when the radiation force is equal to the resisting force exerted by the tissue. In addition, the echoes were displayed in a range indicative of origination in the target. The rf data indicated that acoustic radiation force is adequate to displace target tissue.

It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

What is claimed is:

1. A combined system which synchronizes optical coherence tomography and acoustic radiation force for simultaneously imaging and mechanically displacing interior body tissue in a patient, which comprises:
   an endoscopic probe:
   a piezoelectric transducer located inside the endoscopic probe for delivering acoustic radiation force to a target area of the interior body tissue to mechanically displace the interior body tissue;
   an optical coherence tomography device having a light source located inside the endoscopic probe to provide infrared light, a movable mirror located inside the endoscopic probe to receive the infrared light from said light source, an actuator device located inside the endoscopic probe to move said movable mirror to direct the infrared light from the light source to scan across the target area to illuminate the interior body tissue before and during delivery of the acoustic radiation force by said piezoelectric transducer, and a lens located inside the endoscopic probe to receive images of the target area of the tissue before and during the delivery of the acoustic radiation force as the infrared light scans across the target area of the interior body tissue, and
   a controller for determining a displacement of the target area of the interior body tissue resulting from the delivery of the acoustic radiation force.

2. A method of obtaining mechanical properties of interior body tissue in a patient, comprising simultaneously imaging said interior body tissue using optical coherence tomography while subjecting said interior body tissue to mechanical displacement using acoustic radiation force, and determining a displacement of the interior body tissue resulting from the delivery of the acoustic radiation force.

3. A method of detecting cancer within interior body tissue in a patient, comprising simultaneously imaging said interior body tissue using optical coherence tomography while subjecting said interior body tissue to mechanical displacement using acoustic radiation force, and comparing the imaging and displacement data to known values of healthy and unhealthy tissue properties.

4. A method of detecting whether interior arterial plaque in a patient is solid or liquid filled, comprising simultaneously imaging said interior arterial plaque using optical coherence tomography while subjecting said target tissue to mechanical displacement using acoustic radiation force, and comparing the imaging and displacement data to control data.

5. A system comprising:
   an acoustic radiation force component which is operationally synchronized with an optical coherence tomography component, the acoustic radiation force component comprising an acoustic source and an acoustic detector, the acoustic source and detector being operably connected to a power source, the power source being operably connected to a function generator, and the function generator being operably connected to a controller having data acquisition, storage and analysis capability, the controller having the capability to process acquired acoustic data, make determinations of at least one of acoustic emission properties, induced and intrinsic tissue displacements and relate the determination of at least one of acoustic emission properties, induced and intrinsic tissue displacement with at least one physiological tissue condition of a target tissue, the controller being operably connected to a display device for displaying information relating to the at least one physiological tissue condition, and
   the optical coherence tomography component comprising an apparatus for optical coherence tomography comprising a low coherent light source; an optical fiber interferometer, including a beam-splitter, a sampling and reference optical fiber arms, and a photodetector, which are mutually optically coupled, a data processing and displaying unit, a reference mirror being placed at the end of said reference arm, the output of said photodetector being connected with said data processing and displaying unit, and a source of control voltage, whereas the output of said data processing and displaying unit of said optical fiber interferometer is the output of said apparatus for optical coherence tomography; at least one of said arms comprising an in-depth scanner having a capability of changing the optical length of said arm by at least several tens of operating wavelengths of said light source, said in-depth scanner being controlled by a source of control voltage, said sampling arm including a flexible part, which is made capable of being introduced into an instrumental channel of an endoscope or borescope and being provided with an optical fiber probe; said optical fiber probe being designed miniature and including a lens system.

6. A system of claim 5, wherein a part of said sampling arm of said interferometer, including said part that is made capable of being introduced into an instrumental channel of an endoscope or borescope, is detachably connected with a main part of said sampling arm.

7. A system as claimed in claim 5, wherein said changeable part of said sampling arm of said interferometer is disposable.

8. A system as claimed in claim 5, wherein the distal part of said optical fiber probe is made with changeable tips.

* * * * *